United States Patent [19]

McDonald

[11] Patent Number: 4,463,754
[45] Date of Patent: Aug. 7, 1984

[54] SAFETY CONTROL AND LOCK FOR ANESTHETIC VAPORIZERS

[75] Inventor: Sandy McDonald, Ancaster, Canada

[73] Assignee: Southmedic Incorporated, Ancaster, Canada

[21] Appl. No.: 522,397

[22] Filed: Aug. 11, 1983

[51] Int. Cl.³ .............................................. A61M 16/00
[52] U.S. Cl. ......................... 128/200.14; 128/200.19; 73/483; 137/637.1; 137/635; 251/149.9; 251/111
[58] Field of Search ...................... 128/200.14, 200.19; 74/483 K, 483 R; 137/637.1, 635; 251/149.9, 111

[56] References Cited

U.S. PATENT DOCUMENTS

| | | | |
|---|---|---|---|
| 2,327,047 | 8/1943 | Joyce | 74/483 R |
| 3,039,946 | 6/1962 | Ellis | 137/637.1 |
| 3,389,616 | 6/1968 | Farekas | 74/483 R |
| 4,307,718 | 12/1981 | Schreiber | 128/200.14 |
| 4,308,865 | 1/1982 | Hay | 128/200.14 |
| 4,346,701 | 8/1982 | Richards | 128/200.14 |
| 4,351,327 | 9/1982 | Rinne et al. | 128/200.14 |

Primary Examiner—Henry J. Recla
Attorney, Agent, or Firm—Murray Schaffer

[57] ABSTRACT

A control device for anesthetic vaporizers disclosed herein ensures that the operator is able to select a desired anesthetic with certainty, and to assure that other anesthetic vaporizer apparatus also in use is in an "off" condition when one anesthetic has been selected. The apparatus also includes a setting at which all of a plurality of associated anesthetic vaporizers are safely "off". The invention comprises a rotatable rod adapted for mounting on an assembly of anesthetic vaporizer tanks, the rod having a plurality of C-collars thereon, the opening in each C-collar adapted to receive a flat spiral wing projecting from the on/off control on an anesthetic vaporizer. The C-collars also permit a setting at which it is impossible to open any of the associated anesthetic vaporizers. The control mechanism includes visual indicia as well as an audible indicator when a correct setting has been selected by the operator.

4 Claims, 6 Drawing Figures

SAFETY CONTROL AND LOCK FOR ANESTHETIC VAPORIZERS

The present invention relates to a control device for anesthetic vaporizers as used to anesthetize patients during surgery.

Generally two or more anesthetic gases are available to anesthetists, such as, for example, isoflurane, halothane, and others.

One of the objects of the subject invention is to ensure that the correct anesthetic has been selected, and at the same time to ensure that other vaporizer apparatus is locked in an "off" condition, while one vaporizer is in use. The apparatus also ensures that the operator may have all of the vaporizers in an "off" condition, as required.

A further object of the invention is to provide apparatus which is adaptable for easy physical combination with all of the various types of anesthetic vaporizers in use.

A further object of the invention is to provide good visual indication of the operative or non-operative condition of each of the vaporizers associated with the safety control and lock mechanism which is the subject of this invention.

A further object of the invention is to provide an adaptor for vaporizer apparatus not initially compatible with the control and lock mechanism disclosed herein, which adaptors are easily and quickly mechanically connected to such vaporizers.

A principal object of the invention is to provide a safety control and lock for anesthetic vaporizers comprising: a rod rotatably mounted in a supporting bracket; a plurality of C-collars on said rod adapted for rotation therewith, each C-collar having an opening; means to mount said support bracket on an assembly of anesthetic vaporizer tanks; each of said tanks having a rotatable control knob including a horizontal flat spiral wing adapted to be received in a C-collar on said rod when the opening thereof is in horizontal alignment therewith; said C-collar preventing rotation of said control knob when said opening in said C-collar is not in horizontal alignment with said wing.

These and other objects of the invention will become apparent with reference to the following description.

Reference will now be made to the accompanying drawings in which.

Detailed reference will now be made to the drawings wherein line reference numerals will be used to identify like parts.

Figure 1:
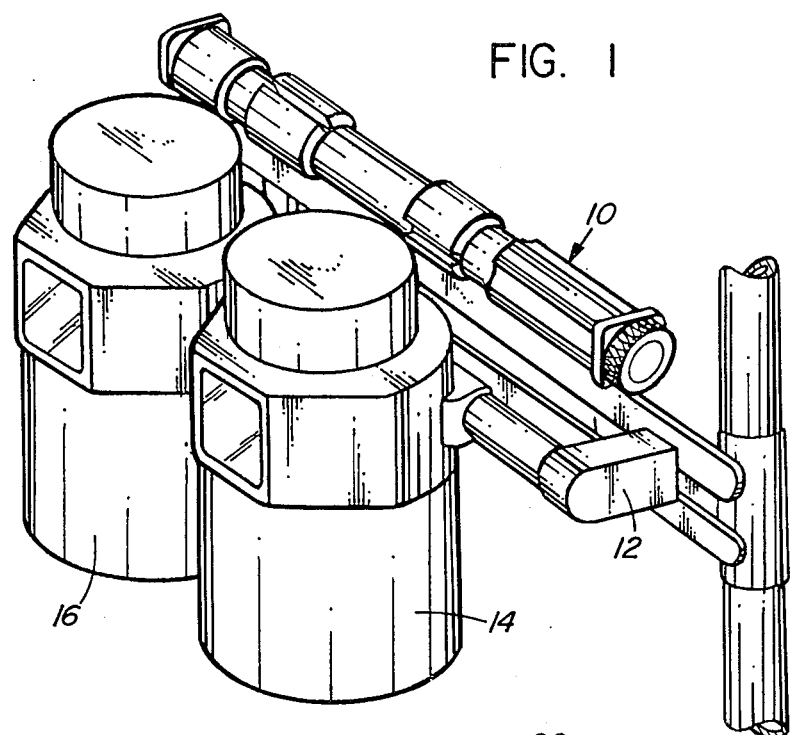
FIG. 1 is a schematic illustration of a control and lock device according to the invention, in association with a pair of anesthetic vaporizers.

Referring to FIG. 1 a safety control and lock is indicated generally at 10, affixed to a support bracket 12 of a pair of anesthetic vaporizers 14 and 16.

Figure 2:
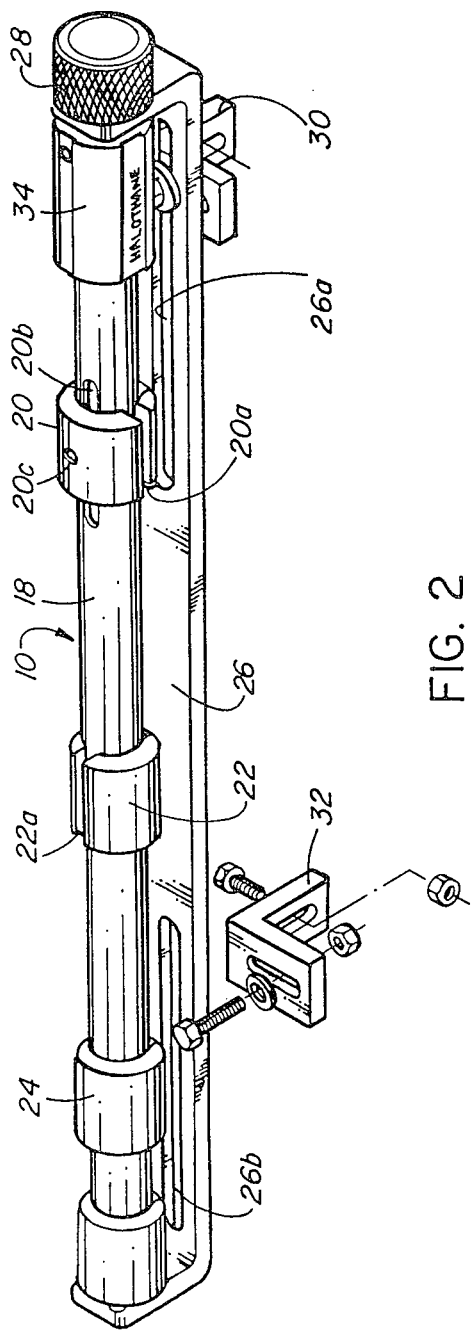
FIG. 2 is an isometric view of a control device according to the invention, with a support bracket shown in exploded view.

Referring to FIG. 2, safety control and lock mechanism 10 comprises a rotatable rod 18 having a plurality of C-collars therearound, three such collars being illustrated in FIG. 2 by reference numerals 20, 22 and 24. Rod 18 is rotatably supported by a U-shaped support bracket 26 and includes a rotatable control knob 28 at one end thereof. Knob 28 may have a knurled surface as illustrated to provide a non-slip surface when grasped by an operator.

U-bracket 26 is in turn supported by a pair of L-brackets 30, 32, adapted for engagement with the bottom of U-bracket 26. As is illustrated in FIG. 2, the bottom of bracket 26 is provided with a pair of elongate slots 26a, 26b, whereby brackets 30 and 32 may be adjusted longitudinally therein, by bolts, or other appropriate attachment means, brackets 30 and 32 permitting the lock-control assembly to be removably affixed to an anesthetic vaporizer apparatus as illustrated schematically in FIG. 1.

At the end of rod 18 adjacent control knob 28 is an indicator collar 34 appropriately marked so as to indicate the setting of the safety control and lock. A more detailed description of the function of indicator collar 34 will follow hereinafter.

Figure 3:
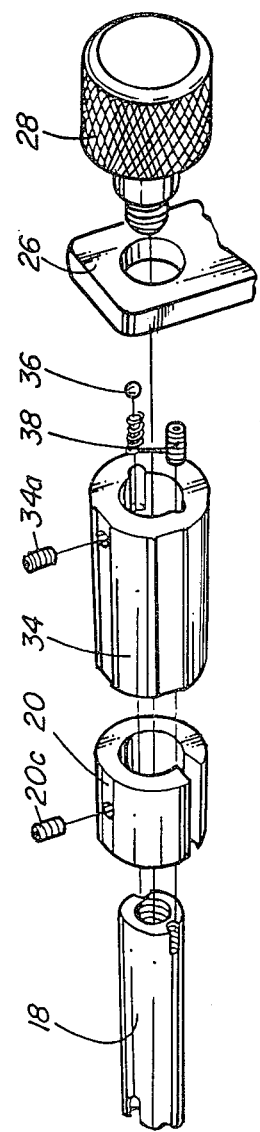
FIG. 3 is an exploded detail of a portion of the control and lock apparatus.

As indicated in FIG. 3, one form of assembly of C-collar 20, indicator collar 34 and control knob 28 on rod 18 is illustrated in exploded view. Also illustrated in FIG. 3 is a spring-loaded ball 36 mounted within the end of indicator collar 34 against the urging of a spring 38, whereby ball 36 is urged against the inner face of the end of U-bracket 26. A plurality of semi-circular indentations are provided in the end of U-bracket 26, so that as rod 18 and its associated collars are rotated manually by rotation of control knob 28, an audible click is heard by an operator, as ball 36 enters each of the indentations provided on the inner face of the end of U-bracket 26. Spring-loaded ball 36 also acts to maintain rod 18 in a selected setting. It will also be seen that collars 20 and 34 are restrained from relative rotation on rod 18 by set screws 20a and 34a, respectively.

Referring to FIG. 2, it will be noted that collar 20 may be longitudinally adjusted on rod 18 by loosening set screw 20c, and a longitudinal indentation 20b is provided in rod 18, to ensure that there is no relative rotation of collar 20 on rod 18.

Figure 4:
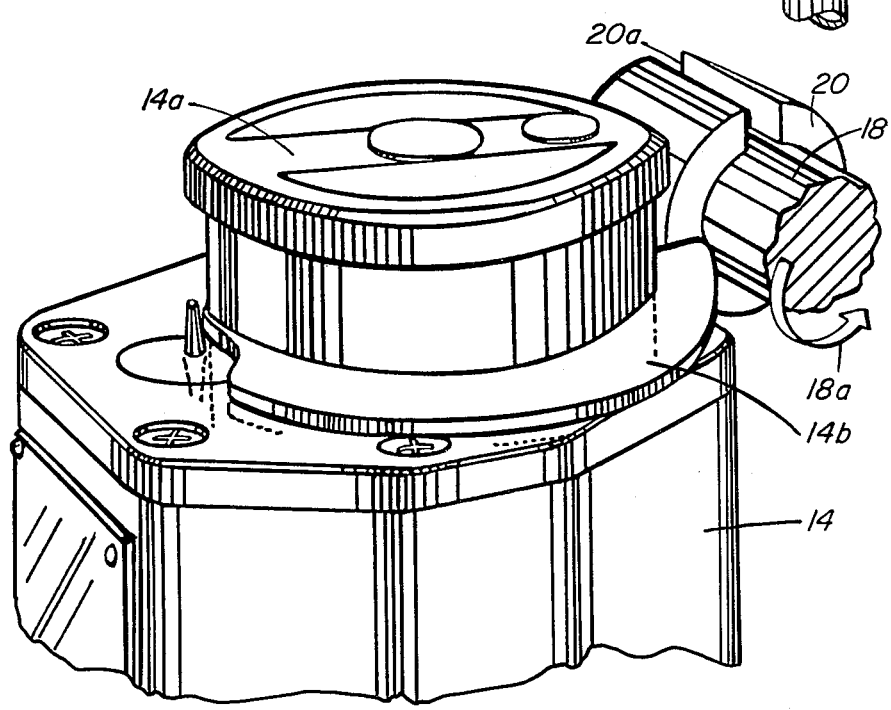
FIG. 4 is an enlarged detail of a portion of the lock-control and a vaporizer control.

Referring to FIG. 4, it will be seen that vaporizer tank 14 has a flow control knob 14a of generally cylindrical configuration, and having a unitary, horizontal flat spiral wing 14b extending outwardly at the base of knob 14a on one side thereof. Wing 14b terminates in a radial end, adapted to butt against collar 20 on rod 18, unless and except C-collar 20 is rotated until opening 20a thereof is in horizontal alignment with wing 14b. In the position illustrated in FIG. 4 control knob 14a is in the "off" position, and can be rotated to an open or flow position only when rod 18 has been rotated in the direction of arrow 18a until opening 20a is horizontally aligned with wing 14b.

Figure 5:
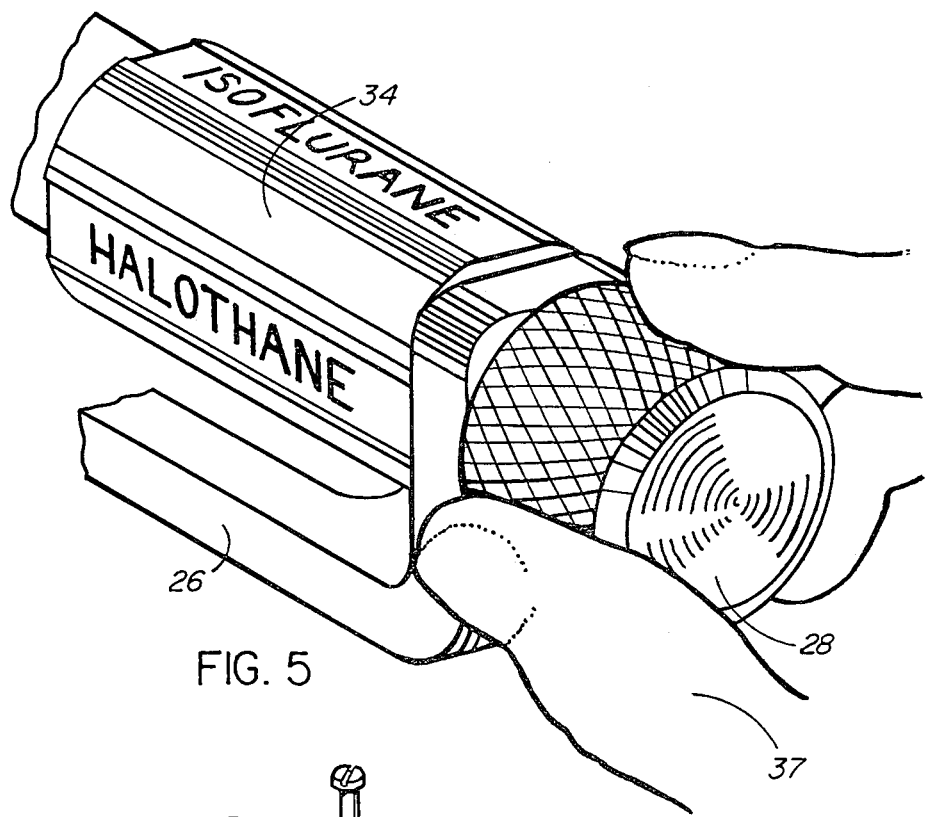
FIG. 5 is an enlarged view of one end of the control according to the invention.

As illustrated in enlarged view in FIG. 5, control knob 28 is being grasped by the fingers of an operator 37, and indicator collar 34 is seen to bear identifying labels "isoflurane" and "halothane", which labels are in longitudinal alignment with the respective openings of control C-collars associated with vaporizer tanks identified thereby. Alternatively, colour coding may be employed, as will be self-evident to those skilled in the art.

Figure 6:
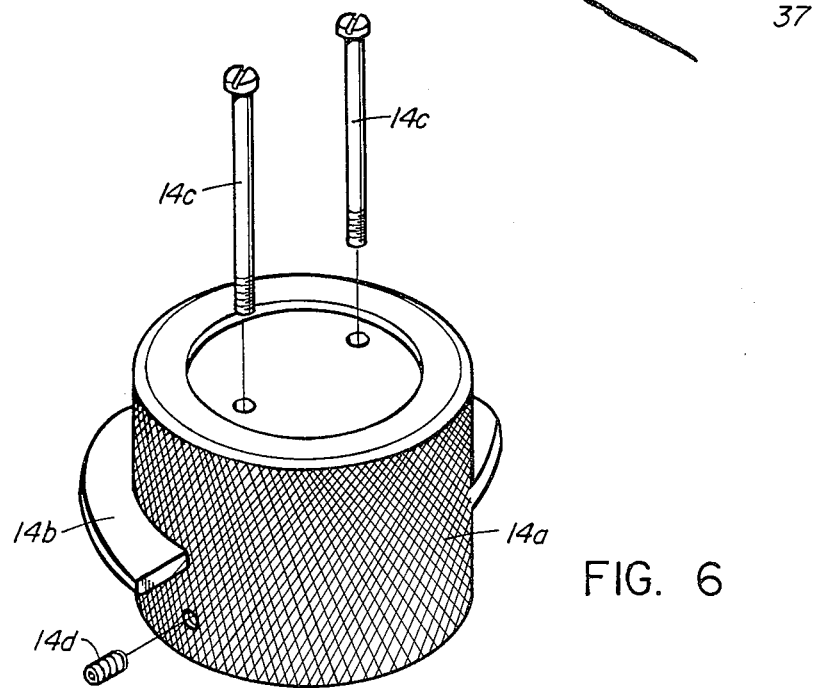
FIG. 6 is a perspective view of an adaptor for use with anesthetic vaporizers.

Illustrated in FIG. 6 is an adaptor knob for use with vaporizer tanks not equipped with circumferential wings 14b, and which may be readily removably affixed to such vaporizer tanks, by means of bolts 14c and/or set screws 14d.

In operation, therefore, it will now be evident that the operator may quickly and conveniently select the anesthetic to be vaporized, by rotation of control knob 28, to the appropriate visual setting, and only then be free to open the vaporizer tank indicated by collar 34. Only one vaporizer may be opened at any time, and referring again to FIG. 2, it will be seen that the openings in C-collars 20 and 22a are 90° apart on rod 18, with collar 24 having its opening a further 90° removed from collar 22. Thus, a setting wherein all vaporizers are in "off" condition is also available.

The foregoing is by way of example only, and the claims should be restricted only by the scope of the appended claims.

The embodiments of the invention in which an exclusive property or privilege is claimed are defined as follows:

1. A safety control and lock for anesthetic vaporizers comprising:
   a supporting bracket;
   a rod rotatably mounted in the supporting bracket;
   a plurality of C-collars, each C-collar mounted around and longitudinally spaced on said rod such as to be rotatable therewith, each C-collar having a longitudinal opening the longitudinal openings of each C-collar being radially offset from each other;
   an assembly of anesthetic vaporizer tanks mounted on said support bracket adjacent each C-collar;
   each of said tanks having a rotatable control knob including a radially extending horizontal flat spiral wing conjointly rotatable therewith into engagement with a C-collar on said rod and receivable in the opening thereof when said opening is rotated into horizontal alignment with said wing;
   said C-collar engaging said wing and preventing rotation of said control knob when said opening in said C-collar is not in horizontal alignment with said wing.

2. A safety control and lock for anesthetic vaporizers according to claim 1, said rod having three C-collars thereon, the opening in each C-collar being separated by 90° from the opening in an adjacent C-collar, whereby a 90° rotation of said rod will selectively align the opening in one of said C-collars with an adjacent anesthetic vaporizer tank control knob, and whereby said rod may be rotated to a position wherein none of said openings in said C-collars is in alignment with its adjacent vaporizer tank control knob.

3. A safety control and lock for anesthetic vaporizers according to claim 2, said rod including a plurality of indicia to indicate which anesthetic vaporizer tank control knob is in alignment with the opening of a C-collar, and further indicia to indicate that none of said anesthetic tank control knobs may be rotated to an open position.

4. A safety control and lock for anesthetic vaporizers according to claim 2, said rod including an internal spring-loaded ball adapted to be engaged with indentations in said bracket, whereby an audible click indicates that the control has been set in a desired position.

* * * * *